US009988445B2

(12) United States Patent
Cook et al.

(10) Patent No.: US 9,988,445 B2
(45) Date of Patent: Jun. 5, 2018

(54) METHOD OF TREATMENT OF PAIN BY ADMINISTRATION OF A CCL17 SPECIFIC ANTIBODY

(71) Applicant: The University of Melbourne, Melbourne, Victoria (AU)

(72) Inventors: Andrew Cook, Melbourne (AU); John Hamilton, Melbourne (AU); Adrian Achuthan, Melbourne (AU); Derek Lacey, Melbourne (AU)

(73) Assignee: THE UNIVERSITY OF MELBOURNE, Melbourne, Victoria (AU)

( * ) Notice: Subject to any disclaimer, the term of this patent is extended or adjusted under 35 U.S.C. 154(b) by 43 days.

(21) Appl. No.: 14/916,141

(22) PCT Filed: Sep. 2, 2014

(86) PCT No.: PCT/AU2014/050203

§ 371 (c)(1),
(2) Date: Mar. 2, 2016

(87) PCT Pub. No.: WO2015/027296

PCT Pub. Date: Mar. 5, 2015

(65) Prior Publication Data

US 2016/0200808 A1 Jul. 14, 2016

(30) Foreign Application Priority Data

Sep. 2, 2013 (AU) ................................ 2013903331

(51) Int. Cl.

| | |
|---|---|
| ***A61K 39/395*** | (2006.01) |
| ***C07K 16/00*** | (2006.01) |
| ***C07K 16/24*** | (2006.01) |
| ***A61K 45/06*** | (2006.01) |
| *A61K 39/00* | (2006.01) |

(52) U.S. Cl.

CPC .......... *C07K 16/24* (2013.01); *A61K 39/3955* (2013.01); *A61K 45/06* (2013.01); *A61K 2039/505* (2013.01); *C07K 2317/76* (2013.01)

(58) Field of Classification Search

None

See application file for complete search history.

(56) References Cited

U.S. PATENT DOCUMENTS

| | | | |
|---|---|---|---|
| 5,942,503 | A | 8/1999 | Jung et al. |
| 2007/0037834 | A1 | 2/2007 | Arai et al. |

FOREIGN PATENT DOCUMENTS

| | | | |
|---|---|---|---|
| WO | WO 00/42074 | A1 | 7/2000 |
| WO | WO 2006/105204 | A2 | 10/2006 |
| WO | WO 2007/069978 | A1 | 6/2007 |

OTHER PUBLICATIONS

Al-Haidari, et al. 2013 "CCR4 mediates CCL17 (TARC)-induced migration of human colon cancer cells via RhoA-Rho-kinase signaling" *International Journal of Colorectal Disease* 28: 1479-1487.

Büyükafşar, et al. 2006 "Rho-kinase inhibitor, Y-27632, has an antinociceptive effect in mice" *European Journal of Pharmacology* 541: 49-52.

Kanai, et al. 2005 "Suppressive activity of epinastine hydrochloride on TARC production from human peripheral blood CD4+ T cells in-vitro" *Journal of Pharmacy and Pharmacology* 57: 1027-1035.

Oh, et al. 2001 "Chemokines and Glycoprotein120 Produce Pain Hypersensitivity by Directly Exciting Primary Nociceptive Neurons" *The Journal of Neuroscience* 21(4): 5027-5035.

Santulli-Marotto, et al. 2013 "Surrogate Antibodies That Specifically Bind and Neutralize CCL17 But Not CCL22" *Monoclonal Antibodies in Immunodiagnosis and Immunotherapy* 32(3): 162-172.

*Primary Examiner* — Christine J Saoud
*Assistant Examiner* — Jon M Lockard
(74) *Attorney, Agent, or Firm* — Knobbe, Martens, Olson & Bear, LLP

(57) ABSTRACT

A protocol for pain management includes a pharmaceutical composition and its use in ameliorating the sensation of pain. The protocol includes the use of a CCL17 signaling antagonist alone or in combination with another analgesic compound to treat pain associated with inflammatory conditions. The CCL17 signaling antagonist includes an antibody or antigen-binding derivative thereof which binds to CCL17 or its receptor.

14 Claims, 1 Drawing Sheet

METHOD OF TREATMENT OF PAIN BY ADMINISTRATION OF A CCL17 SPECIFIC ANTIBODY

FILING DATA

This application is associated with and claims priority from Australian Provisional Patent Application No. 2013903331, filed on 2 Sep. 2013, entitled "A method of treatment", the entire contents of which, are incorporated herein by reference.

BACKGROUND

Field

The present specification teaches a protocol for pain management including a pharmaceutical composition and its use in ameliorating the sensation of pain.

Description of Related Art

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Pain is a debilitating stimulus. The term "pain" covers a spectrum of stimuli including neuropathic, nociceptive, phantom, psychogenic, breakthrough, incident and asymbolia and insensitivity pain.

Pain is a sensory experience associated with actual or potential tissue damage. Pain of any type is the most frequent reason for physician consultation in the United States, prompting half of all Americans to seek medical care annually. It is a major symptom in many medical conditions, significantly interfering with a person's quality of life and general functioning. Diagnosis is based on characterizing pain in various ways, according to duration, intensity, type (dull, burning or stabbing), source or location in body. Acute pain generally stops without treatment or responds to simple measures such as resting or taking an analgesic. However, if it persists and becomes intractable it then becomes chronic pain, in which pain is no longer considered a symptom but an illness by itself.

Of the different pain types, the management of nociceptive and neuropathic pain has been difficult. Stimulation of a nociceptor due to a chemical, thermal or mechanical event that has the potential to damage body tissue leads to nociceptive pain. Damage to a pain nerve itself leads to neuropathic pain.

Although there are numerous therapies available for nociceptor-induced pain, such as treatment with opioid and non-steroidal anti-inflammatory drugs (NSAIDs), these therapies are often unsatisfactory when administration is required over extended time frames due to the emergence of tolerance and adverse side-effects. For example, common side effects of treatment with opioids include constipation, nausea, sedation, respiratory depression, mycolonus, urinary retention, confusion, hallucinations and dizziness. In addition, extended administration typically leads to drug tolerance, resulting in the need for increased levels of drugs to be administered, thereby further exacerbating the side effects of the drugs.

In addition, treatment of neuropathic pain has not met with particular success. This is due to the distinct patho-physiochemical mechanisms and clinical manifestations associated with neuropathic pain relative to pain caused as a result of nociceptor stimulation. Agents useful in the treatment of pain caused as a result of nociceptor stimulation have reduced effectiveness in neuropathic pain treatment. In particular, the effectiveness of opioids in the treatment of neuropathic pain is diminished relative to their use in the treatment of pain caused as a result of nociceptor stimulation. In particular, drug dose response curves for treatment of neuropathic pain are shifted to the right of those for treatment of pain caused as a result of nociceptor stimulation or acute pain.

Accordingly, there is a need to develop safe and efficacious therapies for the short and long term treatment of pain.

SUMMARY

The present specification teaches methods and compositions for treating, alleviating, preventing, diminishing or otherwise ameliorating the symptoms associated with pain including the sensation of pain in a subject. By "symptoms" is meant the perception or sensation of or the physical effects of pain. Reference to "pain" includes neuropathic pain and nociceptive pain as well as pain associated with disease conditions such as inflammation. The latter type of pain is referred to herein as "inflammatory pain".

Enabled herein is the use of compositions and methods comprising a CCL17 signaling antagonist alone or in combination with another analgesic compound in the treatment of pain associated with inflammatory conditions. The term "inflammatory pain" or a pain associated with inflammation is intended to describe the subset of acute and chronic pain that results from inflammatory processes, such as may arise in the case of arthritis, infections and neoplasia or tumor related hypertrophy. Inflammatory pain includes pain associated with osteo-arthritis, rheumatoid arthritis, psoriatic arthropathy, arthritis associated with other inflammatory and autoimmune conditions, degenerative conditions such as back strain and mechanical back pain or disc disease, post operative pain, pain from an injury such as a soft tissue bruise or strained ligament or broken bone, abscess or cellulitis, fibrositis or myositis, Felty's syndrome, Sjogren's syndrome, peripheral neuropathy, biorythmus, bunions, burstis of the knee, Celiac's disease, Cushing syndrome, Costochondritis and Teize's syndrome, dry eyes, ganglion, juvenile idiopathic arthritis (juvenile rheumatoid arthritis), scleritis, relapsing polychondritis, pleurisy, connective tissue disease, steroid drug withdrawal, amyloidosis, uveitis, Raynard's phenomenon, osteopenia, chronic pain, Still's disease, swollen lymph nodes, Lyme disease, gout, sacroliac joint dysfunction, knee pain, lupus and ankle pain. In an embodiment, the pain is neuropathic pain such as but not limited to neuropathic and nociceptive aspects of osteo-arthritic pain.

Other examples of inflammatory conditions associated with pain include, but are not limited to, inflammatory diseases and disorders which result in a response of redness, swelling, pain, and a feeling of heat in certain areas that is meant to protect tissues affected by injury or disease. Inflammatory diseases which include a pain component which can be relieved using the compositions and methods of the present invention include, without being limited to, acne, angina, arthritis, aspiration pneumonia, disease, empyema, gastroenteritis, inflammation, intestinal flu, NEC, necrotizing enterocolitis, pelvic inflammatory disease (PID), pharyngitis, pleurisy, raw throat, redness, rubor, sore throat, stomach flu and urinary tract infections, chronic inflammatory demyelinating polyneuropathy, chronic inflammatory demyelinating polyradiculoneuropathy, chronic inflammatory demyelinating polyneuropathy, chronic inflammatory demyelinating polyradiculoneuropathy.

A method is contemplated herein for inducing an analgesic response to pain in a subject comprising the administration to the subject of an amount of an antagonist of CCL17-mediated signaling, either alone or in combination with an analgesic compound, which administration is effective at reducing the level of or otherwise ameliorating the sensation of pain. In an embodiment, the CCL17 signaling antagonist is an antibody or an antigen-binding derivative thereof which binds to CCL17 or its receptor and which reduces CCL17-mediated signaling. The CCL7 receptor includes CCR4.

Enabled herein is a method for inducing an analgesic response to pain in a subject, the method comprising the administration to the subject of an amount of an antibody or antigen-binding fragment thereof which binds to CCL17 or its receptor which is effective at reducing the level of or otherwise ameliorating the sensation of pain.

Taught herein is a method for inducing an analgesic response to pain in a subject, the method comprising the administration to the subject of an amount of an antibody or antigen-binding fragment thereof which binds to CCL17 or its receptor and an analgesic compound which is effective at reducing the level of or otherwise ameliorating the sensation of pain.

In an embodiment, the synergy between the CCL17 signaling antagonist and the analgesic compound results in less analgesic compound required to be administered and hence less long term adverse effects.

The pain may be neuropathic pain or nociceptive pain and includes inflammatory pain. In an embodiment, the antibody to CCL17 or its receptor is co-administered with an analgesic agent selected from an NSAID, steroid including corticosteroid, anti-inflammatory cytokine (e.g. IL-10), an N-type calcium channel antagonist, an antibody to an inflammatory cytokine (e.g. a GM-CSF antibody), a neuronal excitation inhibitor, a narcotic (e.g. an opioid), an anticonvulsant and a local anesthetic.

Another aspect enabled herein is a method for inducing an analgesic response in a subject suffering from pain, the method comprising the administration of a CCL17 signaling antagonist concurrently, separately or sequentially with an analgesic compound selected from an NSAID, steroid, anti-inflammatory cytokine, a N-type calcium channel antagonist, an antibody to an inflammatory cytokine, a neuronal excitation inhibitor, a narcotic, an anticonvulsant and a local anesthetic in an amount effective to induce an analgesic response. In an embodiment, the CCL17 signaling antagonist is an antibody or antigen-binding fragment thereof which binds to CCL17 or its receptor and reduces CCL17-mediated signaling.

A delivery system is also provided for inducing analgesia in response to pain in a subject comprising a CCL17 signaling antagonist. The delivery system may, for example, be in the form of a cream or an injection. The "injection" includes slow or controlled release injectables. The delivery system may also be a sustained release or slow release formulation, or a tamper proof formulation, or a pharmaceutical formulation or coated onto a stent, catheter or other mechanical device designed for use in a medical procedure.

The compounds according to the methods taught herein may be administered, inter alia, orally, transmucosally, rectally including via suppository, subcutaneously, intravenously, intramuscularly, intraperitoneally, intragastrically, intranasally, transdermally, transmucosally, including rectal, buccal (sublingual), transnasal administration or intestinally or injected into a joint. Further contemplated herein are nanoparticulate formulations which include nanocapsules, nanoparticles, microparticles, liposomes, nanospheres, microspheres, lipid particles, and the like. Such formulations increase the delivery efficacy and bioavailability and reduce the time for analgesic effect of the pain management agents. Nanoparticles generally comprise forms of the agents entrapped within a polymeric framework or other suitable matrix. Nanoparticle formulations are particularly useful for sparingly water soluble drugs. Such formulations also increase bioavailability. One method of formulation is a wet bead milling coupled to a spray granulation.

Methods and compositions are provided herein for use in treating pain.

The CCL17 signaling antagonist such as a CCL17-specific antibody or CCL17 receptor-specific antibody is administered at a dose of between about 50 μg to 2,000 mg, at intervals of between about 1 hour and about 50 hours and may be administered prior to, simultaneously with or following another analgesic compound. These amounts can also be represented in terms of kg of body weight. Hence, doses include 0.5 μg/kg body weight to 20 mg/kg body weight.

In an embodiment, the subject is a mammal including a human. The subject or a group of subjects may be selected on the basis of the type of pain experienced. The "type" of pain may also be subjectively determined based on symptoms described by the subject. Hence, a therapeutic protocol is contemplated herein which comprises selecting a subject on the basis of symptoms of pain and administering to the subject a CCL17 signaling antagonist. In an embodiment, the CCL17 signaling antagonist is an antibody or antigen-binding fragment thereof which binds to CCL17 or its receptor and reduces CCL17-mediated signaling.

Pain management protocols including point of care therapeutic protocols for controlling pain or the sensation of pain are also provided herein. The protocols include assessing a subject for pain type or causation of pain and providing to the subject a CCL17 signaling antagonist alone or in combination with another analgesic compound. The pain may be neuropathic pain or nociceptive pain such as inflammatory pain.

Enabled herein is the use of a CCL17 signaling antagonist in the manufacture of a medicament for the treatment of pain in a subject.

Taught herein is the use of a CCL17-specific antibody or CCL17 receptor-specific antibody or antigen-binding fragment thereof in the manufacture of a medicament for the treatment of pain in a subject.

A CCL17 receptor includes CCR4.

DETAILED DESCRIPTION

Figure 1:
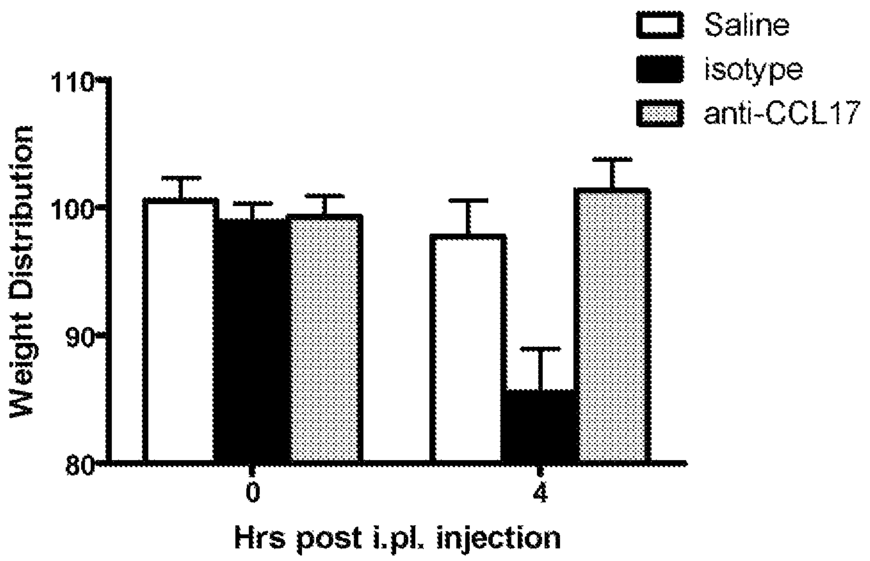
FIG. 1 is a graphical representation showing that antibody to CCL17 (300 μg) given at the same time as GM-CSF (20 ng) intraplantarly (i.pl.) can prevent pain development at 4 hours. Mice received GM-CSF+ isotype control mAb, GM-CSF+anti-CCL17 mAb, or saline i.pl. into one paw and saline into the contralateral paw. Pain is identified as a decrease in the ratio of weight distribution between the GM-CSF-injected and saline-injected paw where a percentage of less than 95 indicates pain development. $P<0.0001$, anti-CCL17 vs. isotype, 4 hours.

Throughout this specification, unless the context requires otherwise, the word "comprise" or variations such as "comprises" or "comprising", will be understood to imply the inclusion of a stated element or integer or method step or group of elements or integers or method steps but not the exclusion of any element or integer or method step or group of elements or integers or method steps.

As used in the subject specification, the singular forms "a", "an" and "the" include plural aspects unless the context clearly dictates otherwise. Thus, for example, reference to "a CCL17 signaling antagonist" includes a single antagonist, as well as two or more antagonists: reference to "an antibody" includes a single antibody, as well as two or more antibody; reference to "the disclosure" includes a single and multiple aspects taught by the disclosure; and so forth. Aspects taught and enabled herein are encompassed by the term "invention". All such aspects are enabled within the width of the present invention.

Terms such as "effective amount", "amounts effective to", "therapeutically effective amount" and "an analgesic effective amount" of an agent as used herein mean a sufficient amount of the agent (i.e. a CCL17 signaling antagonist) to provide the desired therapeutic or physiological effect or outcome, which includes achievement of pain reduction such as a sense of analgesia. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation or the experience of the clinician. The methods and compositions described herein including the therapeutic protocol to achieve analgesia of pain.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, emide, prodrug or derivative of a compound is a salt, ester, amide, prodrug or derivative that this not biologically or otherwise undesirable.

The terms "treating" and "treatment" as used herein refer to reduction in severity and/or frequency of pain associated with a condition being treated, elimination of symptoms and/or underlying cause of the pain, prevention of the occurrence of pain associated with a condition and/or its underlying cause and improvement or remediation or amelioration of pain following a condition. Hence, the treatment proposed herein reduces pain but this may be independent of the condition being treated.

"Treating" a subject may involve both treating the condition and reducing pain.

A "subject" as used herein refers to an animal, including a mammal such as a human who can benefit from the pharmaceutical formulations and methods herein described. There is no limitation on the type of subject that could benefit from the presently described pharmaceutical formulations and methods. A subject regardless of whether a human or non-human animal may be referred to as a subject, individual, patient, animal, host or recipient. The compounds and methods described herein have applications in human medicine, veterinary medicine as well as in general, domestic or wild animal husbandry.

The term "mammal" includes humans and non-human primates such as orangutangs, gorillas and marmosets as well as livestock animals, laboratory test animals, companion animals and captive wild animals. The subject may also be an avian species.

Examples of laboratory test animals include mice, rats, rabbits, simian animals, guinea pigs and hamsters. Rabbits, rodent and simian animals provide a convenient test system or animal model. Livestock animals include sheep, cows, pigs, goats, horses and donkeys.

Taught herein is the use of CCL17-mediated signaling as a target for pain management. Reference to "CCL17-mediated signaling" includes targeting CCL17 or a receptor thereof including CCR4. "CCL17" means chemokine (C-C motif)17 which is also known as thymus- and activation-regulated chemokine. Receptor CCR4 is a G protein coupled receptor. It is proposed herein that an antagonist of a CCL17 or its receptor includes an antibody or antigen-binding fragment thereof, a soluble receptor and a small chemical molecule as well as an agent which inhibits CCL17 or CCR4 or another receptor expression or which promotes degradation of these molecules.

It is proposed that a CCL17 signaling antagonist is useful in the treatment of pain. If used in combination with another analgesic compound, less analgesic compound is required.

Useful antagonists include a CCL17 inhibitor, a CCL17 receptor (e.g. CCR4) inhibitor, a protein expression inhibitor, a degrading agent for CCL17 or its receptor and an antibody to CCL17 or its receptor. In an embodiment, the CCL17 inhibitor is an antibody specific for CCL17 or is a soluble CCL17 receptor.

Enabled herein is a method for inducing an analgesic response to pain in a subject. In this context the term "subject" is intended to include and encompass both humans and non-human animals. This aspect also includes, in an embodiment, the step of selecting a subject having pain to be a recipient of treatment. The selection process includes an assessment of symptoms of pain or symptoms of a condition likely to result in pain.

The term "pain" is intended to describe the subset of acute and chronic pain that results from neuropathic pain or nociceptive pain. Pain from inflammatory conditions is also contemplated.

The term "neuropathic pain" is to be understood to mean pain initiated or caused by a primary lesion or dysfunction within the nervous system. Examples of categories of neuropathic pain that may be treated by the methods of the present invention include monoradiculopathies, trigeminal neuralgia, postherpetic neuralgia, phantom limb pain, complex regional pain syndromes, back pain, neuropathic pain associated with AIDS and infection with the human immunodeficiency virus and the various peripheral neuropathies, including, but not limited to drug-induced and diabetic neuropathies.

Nociceptive pain is caused by activation of nociceptors and includes pain caused by cuts, bruises, bone fractures, crush injuries, burns, or tissue trauma.

Enabled herein is the use of compositions and methods comprising a CCL17 signaling antagonist alone or in combination with another analgesic compound in the treatment of pain associated with inflammatory conditions. The term “inflammatory pain” or a pain associated with inflammation is intended to describe the subset of acute and chronic pain that results from inflammatory processes, such as may arise in the case of arthritis, infections and neoplasia or tumor related hypertrophy. Inflammatory pain includes pain associated with osteo-arthritis, rheumatoid arthritis, psoriatic arthropathy, arthritis associated with other inflammatory and autoimmune conditions, degenerative conditions such as back strain and mechanical back pain or disc disease, post operative pain, pain from an injury such as a soft tissue bruise or strained ligament or broken bone, abscess or cellulitis, fibrositis or myositis, Felty’s syndrome, Sjogren’s syndrome, peripheral neuropathy, biorythmus, bunions, burstis of the knee, Celiac’s disease, Cushing syndrome, Costochondritis and Teize’s syndrome, dry eyes, ganglion, juvenile idiopathic arthritis (juvenile rheumatoid arthritis), scleritis, relapsing polychondritis, pleurisy, connective tissue disease, steroid drug withdrawal, amyloidosis, uveitis, Raynard’s phenomenon, osteopenia, chronic pain, Still’s disease, swollen lymph nodes, Lyme disease, gout, sacroliac joint dysfunction, knee pain, lupus and ankle pain. In an embodiment, the pain is neuropathic pain. In an embodiment, the pain comprises neuropathic and/or nociceptive aspects of osteo-arthritic pain.

Other examples of inflammatory conditions include, but are not limited to, inflammatory diseases and disorders which result in a response of redness, swelling, pain, and a feeling of heat in certain areas that is meant to protect tissues affected by injury or disease. Inflammatory diseases which include a pain component which can be relieved using the compositions and methods of the present invention include, without being limited to, acne, angina, arthritis, aspiration pneumonia, disease, empyema, gastroenteritis, inflammation, intestinal flu, NEC, necrotizing enterocolitis, pelvic inflammatory disease (PID), pharyngitis, pleurisy, raw throat, redness, rubor, sore throat, stomach flu and urinary tract infections, chronic inflammatory demyelinating polyneuropathy, chronic inflammatory demyelinating polyradiculoneuropathy, chronic inflammatory demyelinating polyneuropathy, chronic inflammatory demyelinating polyradiculoneuropathy.

The terms “analgesia” and “analgesic response” are intended to describe a state of reduced sensibility to pain. In another aspect, the sensibility to pain is completely, or substantially completely, removed. To assess the level of reduction of sensibility to pain associated with the analgesia induced by the methods according to the present invention it is possible to conduct tests such as the short form McGill pain questionnaire and/or visual analog scales for pain intensity and/or verbal rating scales for pain intensity and/or measurement of tactile allodynia using von Frey hairs or similar device. These tests are standard tests within the art and would be well known to the skilled person. Hence, a reduction to the sensibility to pain can be represented subjectively or qualitatively as a percentage reduction by at least 10%, at least 20%, at least 50%, at least 70% or at least 85% or at least 95% or above including at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

In an embodiment the CCL17 signaling antagonist is an antibody specific for CCL17 or its receptor. Such an antibody may be of any type, such as a murine (mouse or rat), a chimeric, a humanized or a human antibody. A “human” antibody or functional human antibody fragment is hereby defined as one that is not chimeric (e.g. not “humanized”) and not from (either in whole or in part) a non-human species. A human antibody or functional antibody fragment can be derived from a human or can be a synthetic human antibody. A “synthetic human antibody” is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment is one that is encoded by a nucleic acid isolated from a library of antibody sequences of human origin (i.e. such a library based on antibodies taken from a human natural source).

A “humanized antibody” or functional humanized antibody fragment is defined herein as one that is (i) derived from a non-human source (e.g. a transgenic mouse which bears a heterologous immune system), which antibody is based on a human germline sequence; or (ii) chimeric, wherein the variable domain is derived from a non-human origin and the constant domain is derived from a human origin or (iii) CDR-grafted, wherein the CDRs of the variable domain are from a non-human origin, while one or more frameworks of the variable domain are of human origin and the constant domain (if any) is of human origin.

The term “chimeric antibody” or functional chimeric antibody fragment is defined herein as an antibody molecule which has constant antibody regions derived from, or corresponding to, sequences found in one species and variable antibody regions derived from another species. Generally, the constant antibody regions are derived from, or corresponding to, sequences found in humans, e.g. in the human germ line or somatic cells, and the variable antibody regions (e.g. VH, VL, CDR or FR regions) are derived from sequences found in a non-human animal, e.g. a mouse, rat, rabbit or hamster.

As used herein, an antibody “binds specifically to”, “specifically binds to”, is “specific to/for” or “specifically recognizes” an antigen (here, CCL17 or its receptor) if such antibody is able to discriminate between such antigen and one or more reference antigen(s), since binding specificity is not an absolute, but a relative property. In its most general form (and when no defined reference is mentioned), “specific binding” is referring to the ability of the antibody to discriminate between the antigen of interest (i.e. CCL17 or its receptor) and an unrelated antigen, as determined, for example, in accordance with one of the following methods. Such methods comprise, but are not limited to, Western blots, ELISA, RIA, ECL and IRMA tests and peptide scans. For example, a standard ELISA assay can be carried out. The scoring may be carried out by standard color development (e.g. secondary antibody with horseradish peroxide and tetramethyl benzidine with hydrogenperoxide). The reaction in certain wells is scored by the optical density, for example, at 450 nm. Typical background (=negative reaction) may be 0.1 OD; typical positive reaction may be 1 OD. This means the difference positive/negative can be more than 10-fold.

Typically, determination of binding specificity is performed by using not a single reference antigen, but a set of about three to five unrelated antigens, such as milk powder, BSA, transferrin or the like. Additionally, “specific binding” may relate to the ability of an antibody to discriminate between different parts of its target antigen, e.g. different domains or regions of CCL17 or its receptor or between one or more key amino acid residues or stretches of amino acid residues of CCL17 or its receptor.

Also, as used herein, an “immunoglobulin” (Ig) hereby is defined as a protein belonging to the class IgG, IgM, IgE, IgA, or IgD (or any subclass thereof), and includes all conventionally known antibodies and functional fragments thereof. A “functional fragment” of an antibody/immunoglobulin is defined as a fragment of an antibody/immunoglobulin (e.g. a variable region of an IgG) that retains the antigen-binding region. An “antigen-binding region” or “antigen-binding fragment” of an antibody typically is found in one or more hypervariable region(s) of an antibody, i.e. the CDR-1, -2, and/or -3 regions; however, the variable “framework” regions can also play an important role in antigen binding, such as by providing a scaffold for the CDRs. One class of immunoglobulins for use in the present invention is IgG. “Functional fragments” include the domain of a $F(ab')_2$ fragment, a Fab fragment, scFv or constructs comprising single immunoglobulin variable domains or single domain antibody polypeptides, e.g. single heavy chain variable domains or single light chain variable domains. The $F(ab')_2$ or Fab may be engineered to minimize or completely remove the intermolecular disulphide interactions that occur between the $C_{HI}$ and $C_L$ domains. It is proposed that these fragments bind to CCL17 or its receptor.

An antibody described herein may be derived from a recombinant antibody library that is based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al. (2000) *J. Mol. Biol.* 296:57; Krebs et al. (2001) *J. Immunol. Methods.* 254:67, Rothe et al. (2008) *J. Mol. Biol.* 376:1182 and U.S. Pat. No. 6,300,064 issued to Knappik et al. (2000) supra.

Accordingly, a method is contemplated herein for inducing an analgesic response to pain in a subject, the method comprising the administration to the subject of an amount of a CCL17 signaling antagonist, or a pharmaceutically acceptable salt, derivative, homolog or analog thereof, effective to reduce the level of or otherwise ameliorate the sensation of pain. In another embodiment, a method is provided for inducing an analgesic response to pain, the method comprising the administration to the subject of an amount of an antibody or antigen-binding fragment thereof which binds to CCL17 or its receptor, effective to reduce the level of or otherwise ameliorate the sensation of pain. In yet another embodiment, a method is provided for inducing an analgesic response to pain, the method comprising the administration to the subject of an amount of a soluble CCL17 receptor or CCL17-binding fragment thereof which binds to CCL17, effective to reduce the level of or otherwise ameliorate the sensation of pain.

The CCL17 signaling antagonist may be administered alone or in combination with one or more of an NSAID, steroid (including a corticosteroid), anti-inflammatory cytokine (e.g. IL-10), an N-type calcium channel antagonist, an antibody to an inflammatory cytokine (e.g. a GM-CSF antibody), a neuronal excitation inhibitor, a narcotic (e.g. an opioid), an anticonvulsant or a local anesthetic.

Enabled herein is a method for inducing an analgesic response to pain in a subject, the method comprising the administration to the subject an amount of a CCL17 signaling antagonist in combination with one or more of an NSAID, steroid, anti-inflammatory cytokine (e.g. IL-10), an N-type calcium channel antagonist, an antibody to an inflammatory cytokine, a neuronal excitation inhibitor, a narcotic, an anticonvulsant or a local anesthetic effective to reduce the level of, or otherwise ameliorate, the sensation of pain.

In another aspect, the present invention provides a method for inducing an analgesic response to pain in a subject, the method comprising the administration to the subject an amount of a CCL17-specific antibody or CCL17 receptor-specific antibody or antigen-binding fragment thereof in combination with one or more of an NSAID, steroid, anti-inflammatory cytokine, an N-type calcium channel antagonist, an antibody to an inflammatory cytokine, a neuronal excitation inhibitor, a narcotic, an anticonvulsant or a local anesthetic effective to reduce the level of or otherwise ameliorate the sensation of pain. Still another aspect contemplates a method for inducing an analgesic response to pain in a subject, the method comprising the administration to the subject an amount of soluble CCL17 receptor or a CCL17-binding fragment thereof in combination with one or more of an NSAID, steroid, anti-inflammatory cytokine, an N-type calcium channel antagonist, an antibody to an inflammatory cytokine, a neuronal excitation inhibitor, a narcotic, an anticonvulsant or a local anesthetic effective to reduce the level of or otherwise ameliorate the sensation of pain.

Still another aspect contemplates combination therapy in the treatment of pain wherein the treatment of the disease, condition or pathology is conducted in association with pain management using a CCL17 signaling antagonist such as an antibody or antigen-binding fragment thereof which binds to CCL17 or its receptor and reduces CCL17-mediated signaling.

Yet another aspect contemplates combination therapy in the treatment of pain wherein the treatment of the disease, condition or pathology is conducted in association with pain management using a CCL17-specific antibody or CCL17 receptor-specific antibody or antigen-binding fragment thereof or a soluble CCL17 receptor or a CCL17-binding fragment thereof and an NSAID, steroid, anti-inflammatory cytokine, an N-type calcium channel antagonist, an antibody to an inflammatory cytokine, a neuronal excitation inhibitor, a narcotic, an anticonvulsant or a local anesthetic.

Another aspect is directed to a method for inducing an analgesic response to pain in a subject comprising administering to the subject an amount of a CCL17 signaling antagonist and a local anaesthetic such as lignocaine, bupivacaine, ropivacaine, and procaine tetracaine or a pharmaceutically acceptable salt, derivative, homolog or analog thereof to reduce the level of or otherwise ameliorate the sensation of pain.

Yet another aspect is directed to a method for inducing an analgesic response to pain in a subject comprising administering to the subject an amount of a CCL17-specific antibody or a CCL17 receptor-specific antibody or antigen-binding fragment thereof or a soluble CCL17 receptor or a CCL17-binding fragment thereof and a local anaesthetic such as lignocaine, bupivacaine, ropivacaine, and procaine tetracaine or a pharmaceutically acceptable salt, derivative, homolog or analog thereof to reduce the level of or otherwise ameliorate the sensation of pain.

NSAIDS include, without being limited to, NSAIDS, such as acetaminophen (Tylenol, Datril, etc.), aspirin, ibuprofen (Motrin, Advil, Rufen, others), choline magnesium salicylate (Triasate), choline salicylate (Anthropan), diclofenac (voltaren, cataflam), diflunisal (dolobid), etodolac (Ilodine), fenoprofen calcium (nalfon), flurobiprofen (ansaid), indomethacin (indocin, indometh, others), ketoprofen (orudis, oruvail), ketorolac tromethamine (toradol), magnesium salicylate (Doan's, magan, mobidin, others), meclofenamate sodium (meclomen), mefenamic acid (relafan), oxaprozin (daypro), piroxicam (feldene), sodium salicylate, sulindac (clinoril), tolmetin (tolectin), meloxicam, nabumetone, naproxen, lornoxicam, nimesulide, indoprofen, remifenzone, salsalate, tiaprofenic acid, flosulide, and the like.

Compounds which inhibit neuronal excitation function by reducing, decreasing or blocking pain signals being transmitted to the brain. The term "inhibits" includes "decreases". Herein, these compounds are referred to herein as inter alia "neuronal excitation blockers", "excitation blockers", "neuronal excitation inhibitor" and "antagonists of neuronal excitation". Such compounds include, without being limited to flupirtine or a pharmaceutically acceptable salt, derivative, homolog or analog thereof; retigabine or a pharmaceutically acceptable salt, derivative, homolog or analog thereof; compounds that cause opening of neuronal potassium channels; sodium channel blockers; a modulator of CB2 receptors; a modulator of TRPV1 receptors; a local anaesthetic; opioids; neurosteroids; alpha 2 adrenoceptor antagonists; NSAIDS; NMDA antagonists and calcium channel antagonists. In an embodiment, the CCL17 signaling antagonist and optionally another analgesic compound are administered in amounts effective to reduce the symptoms of inflammatory pain. Such an effective amounts include synergistic effective amounts. In addition, a subject may also be specifically selected on the basis of the type of pain and hence a selection step for a particular patient or subject also forms an aspect enabled herein.

Reference to a "narcotic" includes an opioid. An opioid includes any compound that is physiologically acceptable in animal systems and is a full or at least partial agonist of an opioid receptor. Opioid compounds are well known and include naturally occurring compounds derived from opium such as codeine, morphine and papavarine as well as derivatives of such compounds that generally have structural similarity as well as other structurally unrelated compounds that agonise an opioid receptor present in a mammalian system. Specific examples of opioid compounds contemplated by the present invention include: fentanyl, oxycodone, codeine, dihydrocodeine, dihydrocodeinone enol acetate, morphine, desomorphine, apomorphine, diamorphine, pethidine, methadone, dextropropoxyphene, pentazocine, dextromoramide, oxymorphone, hydromorphone, dihydromorphine, noscapine, nalbuphine papaverine, papaveretum, alfentanil, buprenorphine and tramadol and pharmaceutically acceptable salts, derivatives, homologs or analogs thereof.

The phrase "pharmaceutically acceptable salt, derivative, homologs or analogs" is intended to convey any pharmaceutically acceptable tautomer, salt, pro-drug, hydrate, solvate, metabolite or other compound which, upon administration to the subject, is capable of providing (directly or indirectly) the compound concerned or a physiologically (e.g. analgesically) active compound, metabolite or residue thereof. An example of a suitable derivative is an ester formed from reaction of an OH or SH group with a suitable carboxylic acid, for example $C_{1-3}$alkyl-$CO_2H$, and $HO_2C$—$(CH_2)_n$—$CO_2H$ (where n is 1-10 such as 1, 2, 3, 4, 5, 6, 7, 8, 9, 10, but particularly 1-4), and $CO_2H$—$CH_2$phenyl.

Thus, the active compounds may be in crystalline form, either as the free compounds or as solvates (e.g. hydrates). Methods of solvation are generally known within the art.

The salts of the active compounds used herein are generally pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulfuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulfphonic, toluenesulphonic, benzenesulphonic, salicyclic, sulphanilic, aspartic, glutamic, edetic, stearic, palmitic, oleic, lauric, pantothenic, tannic, ascorbic and valeric acids.

The term "pro-drug" is used herein in its broadest sense to include those compounds which can be converted in vivo to the compound of interest (e.g. by enzymatic or hydrolytic cleavage). Examples thereof include esters, such as acetates of hydroxy or thio groups, as well as phosphates and sulphonates. Processes for acylating hydroxy or thio groups are known in the art, e.g. by reacting an alcohol (hydroxy group), or thio group, with a carboxylic acid. Other examples of suitable pro-drugs are described in Bundgaard *Design of Prodrugs, Elsevier* 1985, the disclosure of which is included herein in its entirety by way of reference.

The compounds used herein may be electrically neutral or may take the form of polycations, having associated anions for electrical neutrality. Suitable associated anions include sulfate, tartrate, citrate, chloride, nitrate, nitrite, phosphate, perchlorate, halosulfonate or trihalomethylsulfonate.

The active agents may be administered for therapy by any suitable route. It will be understood that the active agents are administered in one embodiment via a route that does not result in dose-limiting side effects. Suitable routes of administration may include oral, rectal, nasal, inhalation of aerosols or particulates, topical (including buccal and sublingual), transdermal, vaginal, intravesical and parenteral (including subcutaneous, intramuscular, intravenous, intrasternal, intra-articular, injections into the joint, and intradermal). In one embodiment, administration of the active agent is by a route resulting in first presentation of the compound to the stomach of the subject. In this embodiment, the active agents are generally administered via an oral route. In another embodiment the active agents are administered by the transdermal route. However, it will be appreciated that the route may vary with the condition and age of the subject, the nature of the pain being treated, its location within the subject and the judgement of the physician or veterinarian. It will also be understood that individual active agents may be administered by the same or different distinct routes. The individual active agents may be administered separately or together directly into a joint involved with an inflammatory painful process.

As used herein, an "effective amount" refers to an amount of active agent that provides the desired analgesic activity when administered according to a suitable dosing regime. The amount of active agent is generally an amount that provides the desired analgesic activity. In one aspect, this occurs without causing overt sedation or dose limiting side-effects or drug tolerance. Dosing may occur at intervals of several minutes, hours, days, weeks or months. Suitable dosage amounts and regimes can be determined by the attending physician or veterinarian. For example, a CCL17 antibody or CCL17 receptor antibody may be administered in amounts of about 50 μg to about 2,000 mg including 100 μg, 200 μg, 300 μg, 500 μg, 800 μg, 1,000 μg, 10 mg, 20 mg, 50 mg, 100 mg, 500 mg, 1,000 mg, 1,500 mg and 2,000 mg or an amount in between. Alternatively, the antibody may be administered at a rate of between about 0.5 μg to about 20 mg/kg by body weight every from about 1 hour to up to about 50 hours, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 hours in amounts of 0.5 μg, 1 μg, 10 μg, 100 μg, 1 mg, 10 mg or 20 mg/kg body weight. Useful times include from about 6 hours to about 24 hours, such as 6, 7, 8, 9, 10, 11, 12, 13, 14, 15, 16, 17, 18, 19, 20, 21, 22, 23, 24. Useful times are between from about 12 to about 24 hours, such as 12, 13, 14, 15, 16, 17, 18, 19, 20, 21, 22, 23 or 24 hours. Dosing of the CCL17 signaling antagonist, can be determined by the attending physician in accordance with dosing rates in practice. The administration amounts may be varied if administration is conducted more or less frequently, such as by continuous infusion, by regular dose every few minutes (e.g. 1, 2, 3 or 4 minutes) or by administration every 5, 10, 20, 30 or 40 minutes (e.g. 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 45, 36, 37, 38, 39 or 40 minutes) or every 1, 2, 3, 4, 5, 6, 7, 8, 9, 10, 11, 12, 13, 14, 15, 16, 17, 18, 19, 20, 21, 22, 23 or 24 hours or up to 50 hours such as, for example, 25, 26, 27, 28, 29, 30, 31, 32, 33, 34, 35, 36, 37, 38, 39, 40, 41, 42, 43, 44, 45, 46, 47, 48, 49 or 50 hours. In many instances, administration is conducted simply on the basis of when the patient requires pain relief.

Accordingly, a treatment protocol is contemplated for treating pain in a subject, the protocol comprising the steps of administration to the subject of an effective amount of a CCL17 signaling antagonist.

In another embodiment, a treatment protocol is provided for treating pain in a subject, the protocol comprising the steps of administration to the subject of an effective amount of a CCL17-specific antibody or CCL17 receptor-specific antibody or an antigen-binding fragment thereof.

In another embodiment, a treatment protocol is provided for treating pain in a subject, the protocol comprising the steps of administration to the subject of an effective amount of a soluble CCL17 receptor or a CCL17-binding fragment thereof.

A further aspect also provides a composition comprising a CCL17 signaling antagonist such as a CCL17-specific antibody or CCL17 receptor-specific antibody or an antigen-binding fragment thereof or a soluble CCL17 receptor or a CCL17-binding fragment thereof together with one or more pharmaceutically acceptable additives and optionally other medicaments. The pharmaceutically acceptable additives may be in the form of carriers, diluents, adjuvants and/or excipients and they include all conventional solvents, dispersion agents, fillers, solid carriers, coating agents, antifungal or antibacterial agents, dermal penetration agents, surfactants, isotonic and absorption agents and slow or controlled release matrices. The active agents may be presented in the form of a kit of components adapted for allowing concurrent, separate or sequential administration of the active agents. Each carrier, diluent, adjuvant and/or excipient must be "pharmaceutically acceptable" in the sense of being compatible with the other ingredients of the composition and physiologically tolerated by the subject. The compositions may conveniently be presented in unit dosage form and may be prepared by methods well known in the art of pharmacy. Such methods include the step of bringing into association the active ingredient with the carrier, which constitutes one or more accessory ingredients. In general, the compositions are prepared by uniformly and intimately bringing into association the active ingredient with liquid carriers, diluents, adjuvants and/or excipients or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous phase or non-aqueous liquid; or as an oil-in-water liquid emulsion or a water-in-oil emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent, preservative disintegrant, sodium starch glycollate, cross-linked povidone, cross-linked sodium carboxymethyl cellulose) surface-active or dispersing agent. Moulded tablets may be made my moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for parenteral administration include aqueous and non-aqueous isotonic sterile injection solutions which may contain anti-oxidants, buffers, bacteriostats and solutes which render the composition isotonic with the blood of the intended subject; and aqueous and non-aqueous sterile suspensions which may include suspended agents and thickening agents. The compositions may be presented in a unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. When reconstituted these can be in the form of aqueous solution, dissolved in water, isotonic saline or a balanced salt solution. Additionally, when reconstituted the product could be a suspension in which the compound(s) is/are dispersed in the liquid medium by combination with liposomes or a lipid emulsion such as soya bean.

Compositions suitable for topical administration to the skin, i.e. transdermal administration, may comprise the active agents dissolved or suspended in any suitable carrier or base and may be in the form of lotions, gels, creams, pastes, ointments and the like. Suitable carriers may include mineral oil, propylene glycol, waxes, polyoxyethylene and long chain alcohols. Transdermal devices, such as patches may also be used and may comprise a microporous membrane made from suitable material such as cellulose nitrate/acetate, propylene and polycarbonates. The patches may also contain suitable skin adhesive and backing materials.

The active compounds described herein may also be presented as implants, which may comprise a drug bearing polymeric device wherein the polymer is biocompatible and non-toxic. Suitable polymers may include hydrogels, silicones, polyethylenes and biodegradable polymers.

The CCL17 signaling antagonist may be administered in a sustained (i.e. controlled) or slow release form. A sustained release preparation is one in which the active ingredient is slowly released within the body of the subject once administered and maintains the desired drug concentration over a minimum period of time. The preparation of sustained release formulations is well understood by persons skilled in the art. Dosage forms may include oral forms, implants and transdermal forms, joint injections, sustained or slow release injectables. For slow release administration, the active ingredients may be suspended as slow release particles or within liposomes, for example.

The compositions herein may be packaged for sale with other active agents or alternatively, the CCL17 signaling antagonists may be formulated with another analgesic compound such as an NSAID, steroid, anti-inflammatory cytokine, an N-type calcium channel antagonist, an antibody to an inflammatory cytokine, a neuronal excitation inhibitor, a narcotic, an anticonvulsant, or a local anesthetic or a pharmaceutical salt, derivative, homolog or analog thereof. The composition may be sold or provided with a set of instructions in the form of a therapeutic protocol. This protocol may also include, in one embodiment, a selection process for type of patient or type of condition or a type of pain.

The present invention further contemplates nanoparticulate formulations which include nanocapsules, nanoparticles, microparticles, liposomes, nanospheres, microspheres, lipid particles, and the like. Such formulations increase the delivery efficacy and bioavailability and reduce the time for analgesic effect of the pain management agents. Nanoparticles generally comprise forms of the agents entrapped within a polymeric framework or other suitable matrix. Nanoparticle formulations are particularly useful for sparingly water soluble drugs. Such formulations also increase bioavailability. One method of formulation is a wet bead milling coupled to a spray granulation.

It should be understood that in addition to the ingredients particularly mentioned above, the compositions herein may include other agents conventional in the art, having regard to the type of composition in question. For example, agents suitable for oral administration may include such further agents as binders, sweeteners, thickeners, flavouring agents, disintegrating agents, coating agents, preservatives, lubricants and/or time delay agents.

The formulation may also contain carriers, diluents and excipients. Details of pharmaceutically acceptable carriers, diluents and excipients and methods of preparing pharmaceutical compositions and formulations are provided in Remmingtons *Pharmaceutical Sciences* $18^{th}$ Edition, 1990, Mack Publishing Co., Easton, Pa., USA.

In an embodiment, the active agents may also be presented for use in veterinary compositions. These may be prepared by any suitable means known in the art. Examples of such compositions include those adapted for:

(a) oral administration, e.g. drenches including aqueous and non-aqueous solutions or suspensions, tablets, boluses, powders, granules, pellets for admixture with feedstuffs, pastes for application to the tongue;

(b) parenteral administration, e.g. subcutaneous, intra-articular, intramuscular or intravenous injection as a sterile solution or suspension or through intra-nasal administration; and (c) topical application, e.g. creams, ointments, gels, lotions, etc.

In another embodiment, the active agents are administered orally, preferably in the form of a tablet, capsule, lozenge or liquid. The administered composition may include a surfactant and/or solubility improver. A suitable solubility improver is water-soluble polyethoxylated caster oil such as Cremophor EL. Alternatively, the active agents are formulated in a cyclodextrin.

Mechanical devices are also provided for introduction to or in a body or body cavity coated with a sustained or slow release formulation of a CCL17 signaling antagonist. Examples of mechanical devices include stents, catheters, artificial limbs, pins, needles, intrathecal implants and the like. Reference to an "intrathecal implant" includes reference to a cylindrical thread or device comprising a semi-permeable membrane which permits passage or partial passage of small molecules (such as nutrients ad drugs in and cellular metabolic products out). The implant may also contain genetically modified or cultured cells (including stem cells) which secrete out useful cytokines and other metabolites. The implant may be designed to release molecules (or intake cellular by-products) for days, weeks, months or even years.

Stents, for example, typically have a lumen, inner and outer surfaces, and openings extending from the outer surface to the inner surface. The present invention extends to a method for coating a surface of a stent. At least a portion of the stent is placed in contact with a coating solution containing a coating material to be deposited on the surface of the stent. A thread is inserted through the lumen of the stent, and relative motion between the stent and the thread is produced to substantially remove coating material within the openings.

The thread can have a diameter substantially smaller than the diameter of the lumen. The thread can be inserted through the lumen either after or prior to contacting the stent with the coating solution. Relative motion between the stent and the thread can be produced prior to contacting the stent with the coating solution to clean the stent. The thread can be either a filament or a cable with a plurality of wires. The thread can be made of a metallic or polymeric material.

The stent can be dipped into the coating solution or spray coated with the coating solution. The coating material can include a biocompatible polymer, either with or without a pharmaceutically active compound.

In one embodiment, the relative motion is oscillatory motion produced by a vibrating device. The oscillations can be changed (magnitude and/or frequency) to vary thickness of the coating solution on the stent. In another embodiment, the relative motion is produced by a shaker table. Regardless of the type of motion, the relative motion can be produced either after or while the stent is in contact with the coating solution.

The relative motion between the stent and the thread can include initially moving the stent in a horizontal direction substantially parallel to the length of the thread and subsequently moving the stent in a vertical direction substantially perpendicular to the length of the thread. The movement in the horizontal direction can be repeated, with pauses between repetitions. The movement in the vertical direction can also be repeated, with the horizontal and vertical movements alternating.

In order to smooth the relative motion, the thread can be coupled to a damping compensator. The damping compensator connects the thread to a vibrating device. In one embodiment, the damping compensator comprises first and second filaments connected to the thread.

The relative motion can be motion of the stent along the thread. For example, a first end of the thread can be attached to a first stand at a first height and a second end of the thread is attached to a second stand at a second height. The relative motion is produced by a gravity gradient, with the first height differing from the second height. Furthermore, the stent can be moved back and forth between the first and second stands by sequentially increasing or decreasing at least one of the first and second heights. In this way, multiple coatings can be applied to the stent.

The relative motion can also be rotation of the stent relative to the thread. A stream of gas can be passed along at least a portion of the surface of the stent to rotate the stent relative to the thread. The rotation can also occur in conjunction with other relative motion between the stent and the thread.

An implantable medical device is also provided having an outer surface covered at least in part by an omega conotoxin and a neuronal excitation inhibitor or pharmaceutically acceptable salts, derivative, homolog or analog thereof and optionally an opioid and/or other active agent, a conformal coating of a hydrophobic elastomeric material incorporating an amount of active material therein for timed delivery therefrom and means associated with the conformal coating to provide a non-thrombogenic surface after the timed delivery of the active material.

In an embodiment, the conformal coating comprises an amount of finely divided biologically active material in the hydrophobic elastomeric material.

Enabled herein is the use of a CCL17 signaling antagonist in the manufacture of a medicament for the treatment of pain in a subject.

Taught herein is the use of a CCL17-specific antibody or a CCL17 receptor-specific antibody or antigen-binding fragment thereof in the manufacture of a medicament for the treatment of pain in a subject.

Further taught herein is the use of a CCL17-specific antibody or a CCL17 receptor-specific antibody or antigen-binding fragment thereof in the manufacture of a medicament for the treatment of neuropathic pain in a subject.

Still further taught herein is the use of a CCL17-specific antibody or a CCL17 receptor-specific antibody or antigen-binding fragment thereof in the manufacture of a medicament for the treatment of neuropathic and/or nociceptive aspects of osteo-arthritic pain.

EXAMPLES

Aspects disclosed herein are further described by the following non-limiting Examples.

Example 1

CCL17 Blockade Ameliorates GM-CSF-driven Inflammatory Pain

Mice given the proinflammatory cytokine GM-CSF (20 ng) intraplantarly (i.pl.) in the footpad develop pain at four hours, whereas mice given saline do not. Mice were treated with a monoclonal antibody (mAb) to CCL17 (300 μg) or with an isotype control mAb (300 μg) at the same time as being given GM-CSF and pain was measured at four hours later.

Read Out for Pain

An Incapacitance Tester (Dual Weight Averager) is used to automatically and reproducibly assess the analgesic potency by measuring the weight distribution on the two hind paws. The force exerted by each limb (measured in grams) is averaged over a user selectable period thus indicating any tendency for the animal to shift its weight from one side to another, hence providing a quantitative measurement of pain.

Weight placed on each hind limb was measured over a 3 second period. 3 separate measurements taken per mouse for each time point then averaged. Results are expressed as injected limb/control limb×100. Thus a value of 100 means that equal weight is being placed on the right and the left limb. A value below 100 means less weight is being placed on the injected limb (left) compared with the control limb (right).

Results

Mice given GM-CSF and a mAb to CCL17 i.pl. do not develop pain. Mice given an isotype control mAb with GM-CSF i.pl. still develop pain. This indicates that CCL17 is important for GM-CSF-driven pain development and that its blockade can prevent such pain from developing. The results are shown in FIG. 1.

Example 2

CCL17 Induces Inflammatory Pain

Figure 2:
FIG. 2 is a graphical representation showing that CCL17 (50 ng) given intraplantarly (i.pl.) induces pain at 6 hours ($p<0.05$, CCL17 vs. saline). Mice received CCL17 or saline i.pl. into one paw and saline into the contralateral paw. Pain is identified as a decrease in the ratio of weight distribution between the CCL17-injected and saline-injected paw where a percentage of less than 95 indicates pain development.

Mice given CCL17 (50 ng) intraplantarly develop pain at six hours whereas mice given saline do not. Pain is identified as a decrease in the ratio of weight distribution between the CCL17-injected and saline-injected paw where a percentage of less than 95 indicates pain development (see Example 1 above). Thus, CCL17 can induce pain. The results are shown in FIG. 2.

Example 3

CCL17 Antagonists are Effective in Treating Inflammatory Arthritis Pain

The following experiment would demonstrate that CCL17 antagonists are effective in the treatment of inflammatory arthritis pain. To do so, methylated bovine serum albumin (mBSA)/IL-1 monoarticular arthritis is induced in CCL17 knock-out mice and in control wild-type C57BL/6 mice. Pain is assessed at various time points using an Incapacitance Tester as in Example 1 above.

Induction of Monoarticular Arthritis

Monoarticular arthritis is induced by intraarticular injection of 10 μl of the antigen mBSA (20 mg/ml) in saline into the left knee joint and 10 μl of saline into the contralateral knee joint. 20 μl of IL-1β (250 ng) is subcutaneously administered daily for 3 days. Arthritis and its associated pain typically develop between days 4 and 7 after injection of mBSA; pain resolves by around day 10 and arthritis around day 28. Pain is measured using the Incapacitance Tester on days 2, 3, 4, 5 and 7.

Results

Synovitis is expected in the mBSA-injected knee joints of wild-type mice and not in the corresponding knee joints of CCL17 knock-out mice on day 7.

Wild-type mice are expected to show significantly more pain (as measured by a shift in weight away from the mBSA-injected knee) compared to CCL17 knock-out mice when mBSA/IL-1 monoarticular arthritis is induced.

Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

BIBLIOGRAPHY

Knappik et al. (2000) *J. Mol. Biol.* 296:57

Krebs et al. (2001) *J. Immunol. Methods.* 254:67

Remmingtons *Pharmaceutical Sciences* $18^{th}$ Edition, 1990, Mack Publishing Co., Easton, Pa., USA.

Rothe et al. (2008) *J. Mol. Biol.* 376:1182

The invention claimed is:

1. A method for inducing an analgesic response to pain in a subject in need thereof, said method comprising administering to said subject of an amount of a CCL17 specific antibody effective in reducing the level of or otherwise ameliorating the sensation of pain.

2. The method of claim 1 further comprising administering another analgesic compound.

3. The method of claim 2 wherein the other analgesic compound is selected from the group consisting of an NSAID, steroid, an anti-inflammatory cytokine, an N-type calcium channel antagonist, an antibody to an inflammatory cytokine, a narcotic, an anticonvulsant and a local anesthetic.

4. The method of claim 1, wherein the pain is neuropathic pain.

5. The method of claim 1, wherein the pain is inflammatory pain.

6. The method of claim 5, wherein, the inflammatory pain is associated with osteoarthritis.

7. The method of claim 5 wherein the inflammatory pain is associated with rheumatoid arthritis.

8. The method of claim 1 wherein the CCL17 specific antibody is administered in an amount of about 0.5 μg to about 20 mg per kg of body weight.

9. The method of claim 1 wherein the subject is a human.

10. A method of treating pain associated with a disease or physiological condition in a subject, said method comprising administering to said subject an effective amount of a CCL17 specific antibody.

11. The method of claim 10 wherein the subject is a human.

12. The method of claim 10 wherein the pain is neuropathic pain or inflammatory pain.

13. The method of claim 12 wherein the pain is associated with osteoarthritis.

14. The method of claim 13 wherein the pain is associated with rheumatoid arthritis.

* * * * *